United States Patent
Ooms et al.

(10) Patent No.: US 6,800,780 B2
(45) Date of Patent: Oct. 5, 2004

(54) METHOD FOR PRODUCING CARBOXYLIC ACID BENZYL ESTERS

(75) Inventors: Pieter Ooms, Krefeld (DE); Ursula Jansen, Neuss (DE); Bernd-Ulrich Schenke, Bottrop (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/239,718

(22) PCT Filed: Mar. 19, 2001

(86) PCT No.: PCT/EP01/03141

§ 371 (c)(1),
(2), (4) Date: Sep. 25, 2002

(87) PCT Pub. No.: WO01/72682

PCT Pub. Date: Oct. 4, 2001

(65) Prior Publication Data

US 2003/0125578 A1 Jul. 3, 2003

(30) Foreign Application Priority Data

Mar. 29, 2000 (DE) .......................................... 100 15 659

(51) Int. Cl.$^7$ ............................................... C07C 69/00
(52) U.S. Cl. ........................ 560/129; 560/240; 562/405
(58) Field of Search ............................... 560/129, 240; 562/405

(56) References Cited

U.S. PATENT DOCUMENTS

| 2,030,835 A | 2/1936 | Cox et al. .................... 260/106 |
| 2,197,798 A | * 4/1940 | Gans et al. .................... 560/1 |
| 3,510,511 A | 5/1970 | Conseiller et al. .......... 260/496 |

FOREIGN PATENT DOCUMENTS

| DE | 286 577 | 1/1991 |
| FR | 794715 | 9/1935 |
| JP | 63150245 | 6/1988 |

OTHER PUBLICATIONS

Clark, GS, Perfumer and Flavorist, vol. 12, Sep. 2000.*
Clark, G.S., A Profile: An Aroma Chemical, Benzyl Acetate, Commodity Services International, Inc. Easton, Maryland, Perfumer & Flavorist, vol. 12, Sep.
Chem. Eng. Comm. vol. 100, (month unavailable) 1991, pp. 135–147, Wang et al, "Benzyl Acetate from Phase Transfer Catalyzed Acetate Displacement of Benzyl Chloride".

* cited by examiner

Primary Examiner—Rita Desai
Assistant Examiner—Hector M. Reyes
(74) Attorney, Agent, or Firm—Godfried R. Akorli; Diderico van Eyl

(57) ABSTRACT

Disclosed herein is a process for the preparation of carboxylic acid benzyl esters from dibenzyl ethers, comprising reacting dibenzyl ethers with carboxylic acids in the presence of a homogeneous acidic catalyst.

12 Claims, No Drawings

METHOD FOR PRODUCING CARBOXYLIC ACID BENZYL ESTERS

The invention relates to a process for the preparation of carboxylic acid benzyl esters from dibenzyl ethers.

Benzyl acetate, the main component of jasmin oil, is an important fragrance for the preparation of scent compositions and starting material for the preparation of fruit ethers.

The preparation of benzyl acetate has already been widely reported. Thus, for example, the preparation of benzyl acetate by reacting benzyl alcohol with acetic acid has been known for a long time. Benzyl acetate can also be prepared by reacting benzyl chloride with alkali metal acetates, optionally in the presence of phase transfer reagents (Wang et al., Chem. Eng. Commun. 100, (1991), 135–147). A disadvantage is the formation of salts which have to be disposed of and thus reduce the cost-efficiency of this process.

DD-A5-286 577 describes the preparation of benzyl acetate by reacting dibenzyl ether with acetic anhydride. Disadvantages are the drastic reaction conditions (300° C./20 MPa) and the only moderate yields.

The object was therefore to provide a process for the preparation of carboxylic acid benzyl esters starting from dibenzyl ether, which can be carried out under mild reaction conditions and leads to good yields.

Surprisingly, we have now found a process for the preparation of carboxylic acid benzyl esters from dibenzyl ethers which is characterized in that dibenzyl ethers are reacted with carboxylic acids in the presence of a homogeneous, acidic catalyst.

The dibenzyl ether used in the process according to the invention is an unsubstituted or substituted dibenzyl ether which can, for example, carry one or more substituents from the series branched or straight-chain $C_1$–$C_6$-alkyl, $C_1$–$C_6$-alkoxy, CN, CO($C_1$–$C_6$)-alkyl, $NO_2$ or halogen. Preferred substituents are methyl, methoxy or chlorine. Particular preference is given to using an unsubstituted dibenzyl ether.

In the process according to the invention, dibenzyl ethers or dibenzyl ether/benzyl alcohol mixtures, as are produced, for example, during the preparation of benzyl alcohol from benzyl chloride, can be used. The content of dibenzyl ether in dibenzyl ether/benzyl alcohol mixtures may, for example, be 50 to 100% by weight, preferably 60 to 100% by weight, particularly preferably 70 to 100% by weight.

The carboxylic acids used in the process according to the invention are straight-chain or branched alkyl-, aryl- or aralkylcarboxylic acids which are saturated or unsaturated and contain 1 to 50 carbon atoms, preferably 2 to 30 carbon atoms, particularly preferably 2 to 10 carbon atoms. In the process according to the invention it is possible to use, for example, formic acid, acetic acid, propionic acid, butyric acid, isobutyric acid, valeric acid, isovaleric acid, caproic acid, caprylic acid, lauric acid, myristic acid, stearic acid, oleic acid, acrylic acid, cinnamic acid, phenylacetic acid, benzoic acid or salicylic acid. Very particularly preferred carboxylic acids are acetic acid and propionic acid.

The process according to the invention is preferably carried out with removal of the water formed. It is appropriate to remove the water by distillation or by passing through an inert gas, such as, for example, nitrogen. To remove the water formed, preference is given to using dehydrating agents, for example zeolites, aluminum oxides or clay earths. Particular preference is given to removing the water formed by carrying out the reaction in the presence of the corresponding anhydride of the carboxylic acid used as dehydrating agent. Very particularly preferred anhydrides are acetic anhydride and propionic anhydride.

In the process according to the invention, preference is given to using 2 to 50 equivalents of carboxylic acid, preferably 3 to 30 equivalents, particularly preferably 4 to 20 equivalents, based on dibenzyl ether.

If the process according to the invention is carried out in the presence of the corresponding anhydride of the carboxylic acid used, then preference is given to using 0.1 to 10 equivalents of anhydride, preferably 0.5 to 7.5 equivalents, particularly preferably 1 to 5 equivalents, based on dibenzyl ether. Since one molecule of anhydride used reacts with the uptake of water to give 2 molecules of carboxylic acid, it is possible to use smaller amounts of carboxylic acid in the process according to the invention. Preference is then given to using 1 to 25 equivalents of carboxylic acid, preferably 1.5 to 15 equivalents, particularly preferably 2 to 10 equivalents of carboxylic acid, based on dibenzyl ether.

In the process according to the invention, the homogeneous acidic catalysts used are preferably strong inorganic acids, such as, for example, sulfuric acid, hydrochloric acid, hydrobromic acid, hydroiodic acid, hydrofluoric acid, perchloric acid or phosphoric acid, strong organic acids, such as, for example, trifluoroacetic acid, methanesulfonic acid, ethanesulfonic acid, benzenesulfonic acid, 4-toluenesulfonic acid, chlorosulfonic acid or trifluoromethanesulfonic acid, and Lewis acids, such as, for example, boron trifluoride, aluminum chloride, zinc chloride, tin chloride, titanium chloride or iron chloride. Preferred homogeneous acidic catalysts are sulfuric acid, trifluoromethanesulfonic acid, 4-toluenesulfonic acid and boron trifluoride.

The homogeneous acidic catalyst is preferably used in an amount of from $10^{-5}$ to 1 equivalents, particularly preferably $10^{-4}$ to 1 equivalents, very particularly preferably $5 \times 10^{-4}$ to 1 equivalents, based on dibenzyl ether.

The temperature at which the process according to the invention is carried out is preferably 15 to 200° C., particularly preferably 25 to 190° C., very particularly preferably 30 to 180° C.

If the process according to the invention is carried out over 100° C., it is necessary to work under increased pressure corresponding to the vapor pressure. The gage pressure required is then at least equal to the vapor pressure of the reaction mixture. It may be up to about 50 bar, preferably up to 25 bar.

The process according to the invention is preferably carried out with intensive thorough mixing of the reactants. Intensive thorough mixing can be achieved in various ways known to the person skilled in the art, for example by stirrers, nozzles, baffles, static mixers, pumps, turbulent flows into narrow tubes and by ultrasound.

The process according to the invention is preferably carried out under a customary protective gas, such as nitrogen, helium or argon.

The process according to the invention can be carried out batchwise, continuously or semicontinuously.

The process according to the invention gives carboxylic acid benzyl esters in good yields with high conversion and good selectivity. The process according to the invention can be carried out easily without high expenditure on apparatus.

Thus, for example, the starting materials can be introduced into a reaction vessel together with the catalyst. The reaction preferably takes place with good thorough mixing and in the presence of inert gas. Work-up can be carried out by adding a water-immiscible solvent, preferably toluene, to the reaction mixture. After the organic phase, which comprises the reaction product, has been separated off, it can be separated by distillation.

EXAMPLES

Example 1

99.2 g (0.5 mol) of dibenzyl ether, 300.0 g (5.0 mol) of acetic acid and 1.0 g of conc. sulfuric acid were heated to 100° C. in a flask with baffles and paddle stirrer with vigorous stirring (250 rpm). After a reaction time of 7 hours, the mixture was cooled rapidly, and the organic phase was separated off following the addition of toluene and water, and analyzed by gas chromatography.

The reaction mixture comprised benzyl acetate and dibenzyl ether in the ratio 36 to 57.

Example 2

Example 2 was carried out analogously to example 1. 60.0 g (1.0 mol) of acetic acid were used and the reaction was carried out at 110° C. The reaction time was 5 hours.

The reaction mixture comprised benzyl acetate and dibenzyl ether in the ratio 35 to 57.

Example 3

Example 3 was carried out analogously to example 1. The reaction temperature was 120° C.

The reaction mixture comprised benzyl acetate and dibenzyl ether in the ratio 67 to 25.

Example 4

Example 4 was carried out analogously to example 1. 90.0 g (1.5 mol) of acetic acid and 0.5 g of trifluoromethanesulfonic acid were used.

The reaction mixture comprised benzyl acetate and dibenzyl ether in the ratio 52 to

Example 5

99.2 g (0.5 mol) of dibenzyl ether, 30.0 g (0.5 mol) of acetic acid, 25.5 g (0.5 mol) of acetic anhydride and 1.0 g of conc. sulfuric acid were heated to 100° C. under nitrogen in a flask with baffles and paddle stirrer with vigorous stirring (250 rpm). After a reaction time of 1 hour, the mixture was cooled rapidly, and the organic phase was separated off following the addition of toluene and water, and analyzed by gas chromatography.

The reaction mixture comprised benzyl acetate and dibenzyl ether in the ratio 83 to 3.

Example 6

Example 6 was carried out analogously to example 5. 15.0 g (0.25 mol) of acetic acid were used. The reaction time was 3 hours.

The reaction mixture comprised benzyl acetate and dibenzyl ether in the ratio 32 to 3.

Example 7

Example 7 was carried out analogously to example 5. 6.0 g (0.1 mol) of acetic acid were used; the reaction time was 3 hours.

The reaction mixture comprised benzyl acetate and dibenzyl ether in the ratio 75 to 7.

Example 8

Example 8 was carried out analogously to example 5. 0.1 g of trifluoromethanesulfonic acid were used, the reaction temperature was 25° C.

The reaction mixture comprised benzyl acetate and dibenzyl ether in the ratio 77 to 5.

Example 9

Example 9 was carried out analogously to example 5. 0.5 g of boron trifluoride diethyl etherate was used.

The reaction mixture comprised benzyl acetate and dibenzyl ether in the ratio 74 to 7.

Example 10

Example 10 was carried out analogously to example 5. 37.0 g (0.5 mol) of propionic acid, 65.1 g (0.5 mol) of propionic anhydride and 0.5 g of conc. sulfuric acid were used; the reaction time was 7 hours.

The reaction mixture comprised benzyl acetate and dibenzyl ether in the ratio 73 to 15.

Example 11

Example 11 was carried out analogously to example 1 but using a mixture of 79.3 g (0.4 mol) of dibenzyl ether and 21.6 g (0.2 mol) of benzyl alcohol at 120° C.

The reaction mixture comprised benzyl acetate and dibenzyl ether in the ratio 68 to 27.

Example 12

Example 12 was carried out analogously to example 11 but using 0.5 g of trifluoromethanesulfonic acid.

The reaction mixture comprised benzyl acetate and dibenzyl ether in the ratio 75 to 16.

Example 13 (Comparative Example)

Example 13 was carried out analogously to example 5 but without catalyst. The reaction time was 7 hours.

The reaction mixture comprised benzyl acetate and dibenzyl ether in the ratio 1 to 94.

Example 14

Example 14 was carried out analogously to example 5. The reaction temperature was 110° C., the reaction time 4 hours. For work-up, the mixture was neutralized with sodium carbonate, filtered and separated by distillation. At 96 to 98° C./22 mbar 108.0 g (72%) of benzyl acetate with a purity of 99.5% were isolated. Before runnings and after-runnings comprised a further 19.0 g (13%) of benzyl acetate.

What is claimed is:

1. A process for the preparation of carboxylic acid benzyl esters from dibenzyl ethers, comprising reacting dibenzyl ethers with carboxylic acids in the presence of a homogeneous acidic catalyst and the corresponding anhydride of the carboxylic acid used.

2. The process as claimed in claim 1, wherein the homogeneous acidic catalyst used is an inorganic acid, an organic acid or a Lewis acid.

3. The process as claimed in claim 1, wherein the homogeneous acidic catalyst used is sulfuric acid, trifluoromethanesulfonic acid, 4-toluenesulfonic acid or boron trifluoride.

4. The process as claimed in claim 1, wherein the dibenzyl ether is unsubstituted dibenzyl ether.

5. The process as claimed in claim 1, wherein the dibenzyl ether is a substituted dibenzyl ether which carries one or more substituents from the series $C_1$–$C_8$-alkyl, $C_1$–$C_6$-alkoxy, CN, CO($C_1$–$C_8$-alkyl). NO2 or halogen.

6. The process as claimed in claim 1, wherein dibenzyl ether is used in a mixture with benzyl alcohol.

7. The process as claimed in claim 1, wherein 2 to 50 equivalents of carboxylic acid, based on dibenzyl ether, are used.

8. The process as claimed in claim 1, wherein, wherein the reaction is carried out with removal of the water formed.

9. The process en claimed in claim 8, wherein the water formed is removed by distillation or by passing through an inert gas.

10. The process as claimed in claim 1, wherein 0.1 to 10 equivalents of anhydride, based on dibenzyl ether, are used.

11. The process as claimed in claim 1, wherein $10^{-5}$ to 1 equivalent of catalyst, based on dibenzyl ether, are used.

12. The process as claimed in claim 1, wherein the reaction is carried out at a temperature of from 15 to 200° C.

* * * * *